United States Patent
Van Der Linden

(10) Patent No.: US 10,869,973 B2
(45) Date of Patent: Dec. 22, 2020

(54) DEVICE FOR THE SUPPLY OF A GAS TO CREATE A PROTECTING ATMOSPHERE

(75) Inventor: Jan Van Der Linden, Saltsjobaden (SE)

(73) Assignee: CARDIA INNOVATION AB, Saltsjobaden (SE)

(*) Notice: Subject to any disclaimer, the term of this patent is extended or adjusted under 35 U.S.C. 154(b) by 1382 days.

(21) Appl. No.: 13/814,062

(22) PCT Filed: Aug. 6, 2010

(86) PCT No.: PCT/EP2010/061499
§ 371 (c)(1),
(2), (4) Date: Apr. 9, 2013

(87) PCT Pub. No.: WO2012/016599
PCT Pub. Date: Feb. 9, 2012

(65) Prior Publication Data
US 2013/0226074 A1  Aug. 29, 2013

(51) Int. Cl.
| A61M 13/00 | (2006.01) |
| A61B 90/40 | (2016.01) |
| A61B 17/00 | (2006.01) |
| A61B 46/00 | (2016.01) |
| A61B 17/34 | (2006.01) |

(52) U.S. Cl.
CPC .............. A61M 13/00 (2013.01); A61B 90/40 (2016.02); A61B 17/3474 (2013.01); A61B 46/00 (2016.02); A61B 2017/00862 (2013.01); A61B 2090/401 (2016.02); A61B 2217/005 (2013.01)

(58) Field of Classification Search
CPC ............... A61M 13/00; A61M 13/003; A61M 2202/0225; A61M 2202/0208; A61M 2202/021; A61M 13/006; A61B 2090/401; A61B 90/40; A61B 46/00
See application file for complete search history.

(56) References Cited

U.S. PATENT DOCUMENTS

| 2,305,289 A * | 12/1942 | Coburg ................. A61B 90/40 128/850 |
| 5,015,243 A * | 5/1991 | Schifano ................ A61B 18/00 604/315 |
| 5,636,643 A | 6/1997 | Argenta et al. |
| 5,645,081 A | 7/1997 | Argenta et al. |

(Continued)

Primary Examiner — Rebecca E Eisenberg
Assistant Examiner — Weng Lee
(74) Attorney, Agent, or Firm — Greer, Burns & Crain, Ltd.

(57) ABSTRACT

A device and use thereof for supply of gas to an operational space configured to adjoin a temporarily open inner portion of a mammal during surgical operations. The device includes a supply conduit, connectable to the gas source including an outlet end, and a body having at least partly an annular shape extending along a circumferential path around centre axis enclosing the operational space. The body has an inner side, outer side, an open interior channel, and an opening allowing the gas to enter the body from the supply conduit. The body is manufactured in foam rubber-like material having large number of open cells functioning as supply nozzles permitting the supply of a substantially laminar, continuous gas stream into the operational space enabling the formation of a gas cushion in the operational space.

12 Claims, 2 Drawing Sheets

(56) References Cited

U.S. PATENT DOCUMENTS

| | | |
|---|---|---|
| 6,494,858 B1 | 12/2002 | van der Linden |
| 6,695,823 B1 | 2/2004 | Lina et al. |
| 7,549,973 B2 * | 6/2009 | Van Der Linden .... A61B 90/40 |
| | | 604/23 |
| 2003/0060750 A1 | 3/2003 | Van Der Linden |
| 2005/0119607 A1 | 6/2005 | Van Der Linden et al. |
| 2006/0174889 A1 * | 8/2006 | Noble .................. A61M 16/01 |
| | | 128/206.11 |
| 2006/0206051 A1 * | 9/2006 | Hamilton ............... A61B 46/23 |
| | | 604/24 |

* cited by examiner

DEVICE FOR THE SUPPLY OF A GAS TO CREATE A PROTECTING ATMOSPHERE

BACKGROUND

The present invention relates to a device for the supply of a gas according to the pre-characterizing portion of claim 1. The invention also relates to a use of the device.

Surgical operations, especially where an inner part of the body is laid open, always create a risk for infections due to the fact that the protective skin has been removed and microorganisms such as bacteria can enter the body of a mammal. In some operations such as heart surgery exposing vessels to air may even lead to embolism. It is thus desired to create a protection layer around the open inner portion of the body to prevent microorganisms and air from entering the unprotected body.

Several devices have been developed, which provide a cushion of a gas over the open inner portion of the body, thereby preventing air to enter the body. Carbon dioxide is a preferred gas because it has bacteriostatic properties. Mixtures of gases and anti-bacterial or anti-viral medicaments mixed in the gases have also been suggested.

EP 1 032 322 describes a device for producing an atmosphere in a region, which adjoins an open inner portion of a body during a surgical operation. The device comprises a gas supply conduit connected to a gas source and a gas supply body arranged in such a way that the gas forces air away from the open portion and prevents air from penetrating the area of the open portion. This gas supply body comprises a plurality of separate nozzles, which provide the gas flow to the open area. The device has a predetermined size and shape and may be ring-shaped, funnel-shaped or a hose.

WO 2006/094062 also describes a device for the supply of gas to an operational space. The device comprises of a ring shaped gas conduit, which has a plurality of separate gas outlets evenly spaced along the gas conduit. Flow limiters may be attached to the separate gas outlets inside the gas conduit, to regulate the gas flow into the operational space.

SUMMARY

The object of the invention is to develop an improved device for delivering a gas to create a protective gas cushion.

Furthermore, the object is a device that can be manufactured in an easy way at low costs and that exhibits a reliable function. It is also aimed at a device that can be flexibly adjusted to the shape of the open inner portion of the mammal body being operated. Furthermore, it is important that the device is dentable without loosing its gas supply function during operation.

This object is achieved by the device initially defined and which is characterised in that the gas supplying body is manufactured in foam rubber-like material having a large number of open cells functioning as supply nozzles permitting the supply of a substantially laminar, continuous gas stream into the operational space enabling the formation of a gas cushion in the operational space.

The predetermined shapes of the known devices may be impractical. For example, during heart surgery a large area may need to be protected, while for surgery on a hand the area to be protected will be relatively small. Furthermore, the known devices are difficult to adapt to operation on an open inner portion located at a high position, such a as a knee or a hip. By the proposed annular body of the foam rubber-like material, the device can be bent into a shape desired for each particular operation. This is especially important for operations on knees, hips and shoulders, where the open inner portions of the body are not in one plane area and vary in heights and sizes.

Further, a surgeon operating on the body may during the operation press against the gas supply body with his hands or arms. When this happens, the gas flow from the gas supply body to the open inner portion of the body should be ensured thanks to the foam rubber-like material. Furthermore, such a material provides a gas supply body that will not be too hard to cause an inconvenience for the surgeon.

The device of the present invention thus overcomes the drawbacks mentioned above.

The device of the present invention is relatively easy to manufacture at low cost in contrast to some of the more complex devices known in the prior art. Advantageously, the body has a drainage opening permitting blood and other possible liquids to be drained from the operational space.

In one embodiment, the device includes a pliable cover member, covering at least a part of the outer side of the body. With such a cover member, the direction of the gas flow inwardly towards the open inner portion is ensured and the flexibility of the device may be maintained. The drainage opening may extend also through the pliable cover member.

In another embodiment, the pliable cover member includes a surface and a passage extending through the surface and the pliable cover member, whereby the outer side of the body is attached to said surface.

In a further embodiment, the pliable cover member includes a sleeve, which extends outwardly away from the body and which is connected to the outlet end and wherein the passage extends through the sleeve.

In one embodiment, the surface of the pliable cover member covers at least 90% of the circumferential length of the body.

In an alternative embodiment, the surface of the pliable cover member covers 10 to 75% of the body in a radial section with respect to the centre axis x.

In yet another embodiment, the body is substantially circular in a radial section with respect to the centre axis x.

In yet a further embodiment, the device includes a stiffening member of a plastically deformable material. Such a stiffening member permits bending of the body to any suitable shape adapted to the specific body part of the mammal to be operated.

In one embodiment, the stiffening member extends in parallel with the circumferential path of the body.

In another embodiment, the stiffening member enables plastic deformation of the annular shape of the body to adapt to positioning of the operational space in or at various body parts of the mammal. This makes the device of the present invention even more suited to be used for surgeries where the operational space is not in one plane such as surgery on hips, knees and shoulders.

In a further embodiment, the stiffening member is embedded in the body.

In an alternative embodiment, the stiffening member is a metal wire.

In yet another embodiment, the foam rubber-like material includes poly-urethane foam. Such a foam rubber-like material of the body has a low weight and is easy to handle.

In one embodiment, the devices comprises at least one attachment member configured to hold the device adjoined to the open inner portion during surgical operations.

In another embodiment, a draping sheet is attached to the device.

In a further embodiment, the gas comprises, or is carbon dioxide. Carbon dioxide may thus be the main component of the gas, which further comprises suitable additives.

The present invention also relates to a use of the device as described herein, for the treatment and/or prevention of infections in an open inner portion of a mammal. The device may also be used for the prevention of growth of microorganisms in an open inner portion of a mammal.

DETAILED DESCRIPTION

Figure 1:
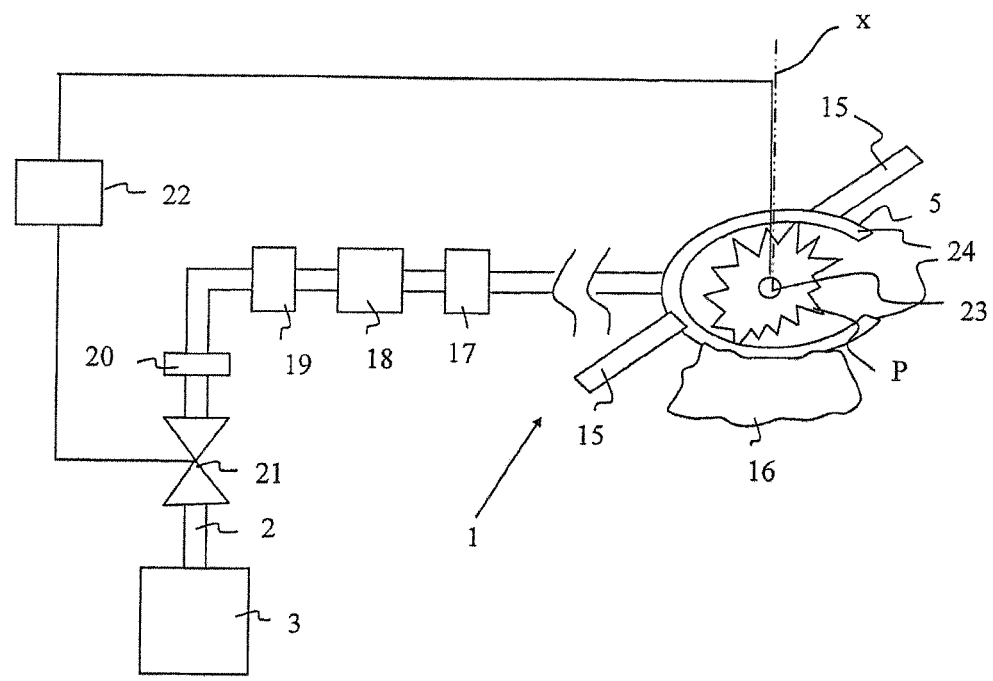
FIG. 1 shows a schematic view of a device according to an embodiment of the invention.

FIG. 1 shows a device 1 for the supply of a gas from a gas source 3 to an operational space P configured to adjoin a temporarily open inner portion of a mammal during surgical operations. The device 1 comprises a supply conduit 2, which is connectable or connected to a gas source 3 and includes an outlet end 4.

The device 1 further comprises a body 5 having at least partly an annular shape extending along a circumferential path around a centre axis x, whereby the body 5 encloses the operational space. The body 5 has an inner side 6 facing the operational space, and an outer side 7, see FIG. 2. Furthermore, the body 5 comprises or encloses an open interior channel 8 extending in parallel with the circumferential path. The body 5 also comprises an opening to allow the gas to enter the interior channel 8 of the body 5 from the supply conduit 2.

The body 5 is manufactured in foam rubber-like material having a large, or very large, number of open cells functioning as supply nozzles permitting the supply of a substantially laminar, continuous gas stream into the operational space P enabling the formation of a gas cushion in the operational space P. The foam rubber-like material of the body 5 may include solely or partly poly-urethane foam. Such a foam rubber-like material is dentable and flexible, and may thus be deformed to any desirable shape.

Figure 2:
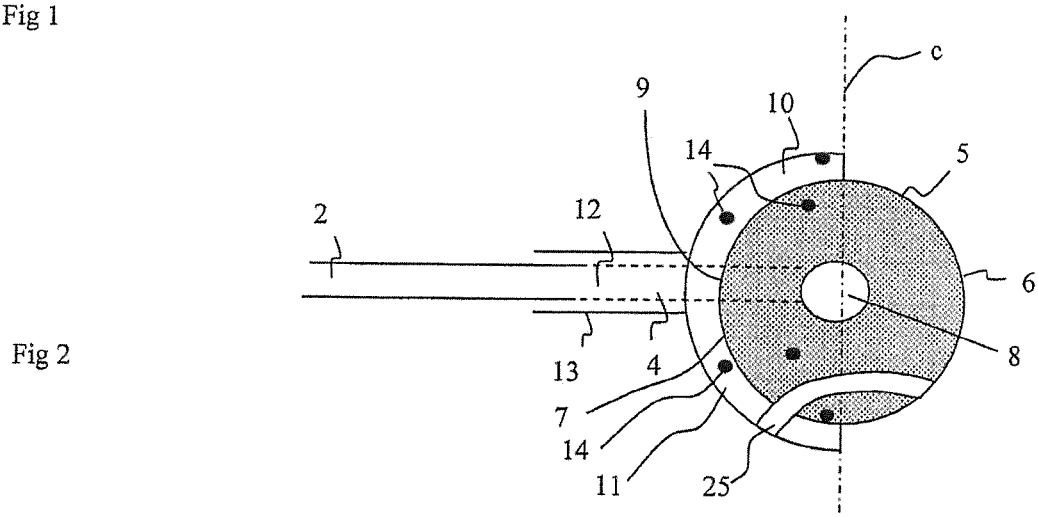
FIG. 2 shows a schematic view of a circular body and a pliable cover member of the device in FIG. 1 in a radial section.

The device 1 may further include a pliable cover member 10, covering at least a part of the outer side 7 of the body 5. The pliable cover member 10 may cover the whole outer side 7 of the body 5 as can be seen in FIG. 2. The pliable cover member 10 may also cover the outer side 7 and part of the inner side 6 of the body 5, or a part of the outer side 7 in a circumferential direction and/or radial direction.

The pliable cover member 10 may include a surface 11 and a passage 12 extending through the surface 11 and the pliable cover member 10, whereby the outer side 7 of the body 5 is attached to said surface 11, for instance by being glued or melted to the surface 11 of the cover member 10.

The pliable cover member 10 may further include a sleeve 13, which extends outwardly away from the body 5 and which is connected to the outlet end 4. The passage 12 extends through the sleeve 13.

The pliable cover member 10 may be manufactured from a deformable material. Thus, the pliable cover member 10 is dentable or flexible, and will not limit the deformability of the body 5.

The centre axis x is shown in FIG. 1. In FIG. 2, the body 5 is shown in a radial section with respect to the centre axis x, together with the inner side 6 and the outer side 7, separated along the longitudinal line c.

If a pliable cover member 10 is present, the surface 11 of the pliable cover member 10 may cover at least 90% of the circumferential length of the body 5. The surface 11 may also cover 100% of the circumferential length of the body 5.

If a pliable cover member 10 is present, the surface 11 of the pliable cover member 10 may cover 10 to 75% of the body 5 seen in a radial section with respect to the centre axis x. The surface 11 may also cover 25 to 75%, or 25 to 50%, or 50% to 75% of the body 5 in a radial section with respect to the centre axis x.

Figure 3A:
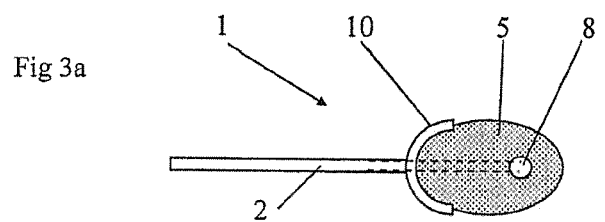
FIGS. 3a-c show alternative shapes of the device.
Figure 3B:
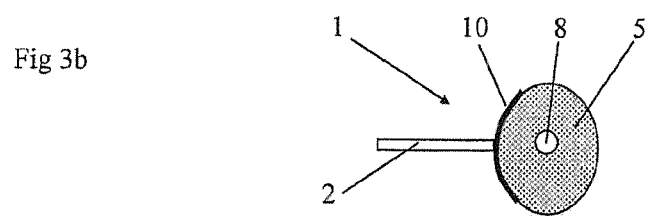

The body 5 may have any applicable shape seen in a radial section. Some variations of possible shapes of the body 5 are shown in FIG. 3. In one embodiment, the body 5 is substantially circular in a radial section with respect to the centre axis x. The body 5 may also be substantially oval in a radial section with respect to the centre axis x. In these embodiments, the body 5 has an inner side 6 and an outer side 7 which each cover 50% of the body 5 in a radial section with respect to the longitudinal line c as shown in FIG. 2.

Figure 3C:
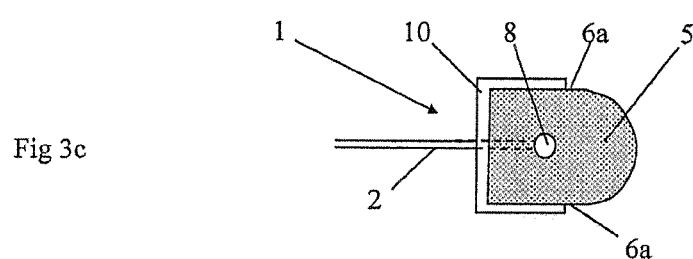

If the shape of the body 5 is partly square in a radial seqtion, as for example shown in FIG. 3c, the outer side 7 is separated from the inner side 6 by upper and lower intermediate sides 6a.

Figure 4A:
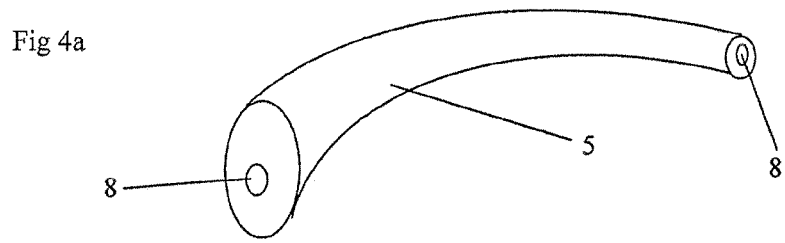
FIGS. 4a, b show alternatives to the annular shape of the body.
Figure 4B:
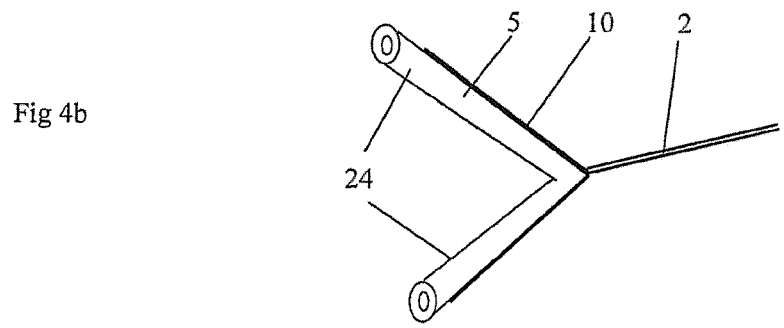

The body 5 may be shaped in any form to surround the operational space. The annular shape of the body 5 may be an open or closed ring. Especially in the latter case, a drainage opening 25, see FIG. 2, may extend through the body 5, and if applicable through the possible cover member 10, for drainage of blood from the operational space P. The outer shape of body may be homogenous in the sense that the surface is substantially uniform. However, the outer shape may also vary, depending on the contours of the open inner portion of the body of the mammal. FIGS. 4a and 4b shows some configurations which the body 5 may have such as rectangular as well as hooter-shaped.

Also shown in FIGS. 3a-c and 4b, b is the open interior channel 8, which may be located centrally in the body 5. This channel 8 however may also be located elsewhere in the body 5, for example closer to the inner side 6 or closer to the outer side 7 of the body 5 and/or above or under the centre of the body 5, seen in a radial section with respect to the centre axis x. Furthermore, the diameter of the open interior channel 8 may vary. The ratio between the diameter of the open interior channel 8 and the diameter of the body 5 may be from 1:10 to 1:2, or 1:5, or 1:4, or 1:3.

The open interior channel 8 may run over the whole circumferential length of the body 5. If the body 5 is shaped as a closed ring, the open interior channel 8 will be continuous over the circumferential length of the circular body 5.

In an other shape of the body 5, for example an open annular shape, the open interior channel 8 may extend to the end part 24 of the body 5 as shown in FIGS. 4a, b. In this embodiment, gas will flow through the open interior channel 8 into the atmosphere. At the end parts 24 of the body 5 the gas from the open interior channel 8 will form an additional cushion of gas at the end parts 24 of the body 5. Alternatively, the open interior channel 8 does not extend to the end part 24 of the body 5. In this embodiment the open interior channel 8 may cover at least 90% of the circumferential length of the body 5.

Only one device 1 may be needed per operation. However, more than one device 1 may be used to surround the operational space, whereby the devices 1 together enable the formation of a gas cushion.

The device 1 may also include a stiffening member 14 of a plastically deformable material. The pliable cover member 10 or the body 5 may include the stiffening member 14. It is also possible for both the pliable cover member 10 and the body 5 to include such a stiffening member 14. The stiffening member 14 may be embedded in the body 5 and/or the pliable cover member 10. The stiffening member 14 may also be provided between the body 5 and the cover member 10. For example a sheet of parallel wires may be placed between the pliable cover member 10 and the body 5. The circumferential length of the stiffening member 14 may vary. The stiffening member 14 can have the same circumferential length as the body 5. The stiffening member 14 may cover at least 90% of the circumferential length of the body 5.

The stiffening member 14 enables plastic deformation of the annular shape of the body to adapt to positioning of the operational space P in or at various body parts of the mammal. The stiffening member 14 is thus deformable without any substantial elasticity. The stiffening member 14 has the capacity of remaining in the shape to which it is bent. The stiffening member 14 may include or be manufactured of a metal wire, for instance stainless steel.

For example, the pliable cover member 10 and/or the body 5 may include 1 to 10 stiffening member 14 such as for example metal wire(s). Preferably, the stiffening member 14 extends in parallel with the circumferential path of the body 5. When the body 5 is formed by an open ring or open structure as shown in FIGS. 4a and 4b, the end parts 24 may be positioned so that they overlap, thereby creating a closed structure.

The device 1 may comprise at least one attachment member 15 configured to hold the device 1 adjoined to the open inner portion P during surgical operations. The attachment member 15 may for example be a tape or a band. The attachment member 15 may be attached to the device 1 in any applicable way. The attachment member 15 may be attached to the outer side 7 of the body 5 and/or the pliable cover member 10. For example, 1, 2, 3, 4 or 5 attachment member 15 may be attached to the device 1, the body 5 and/or the pliable cover member 10.

Also, a draping sheet 16 may be attached to the device 1. This draping sheet 16 may be attached to the outer side 7 of the body 5 and/or the pliable cover member 10. The size of the draping sheet 16 may vary, depending on the type of operation and the size and shape of the operational space.

The pliable cover member 10 may function as a shielding element preventing the gas from flowing away from the operational space P. It may be possible to extend the pliable cover member 10 beyond the body 5 upwardly or downwardly in order to increase the size of the shielding element in order to enhance the closure of the operational space P.

The supply conduit 2 may be manufactured in a flexible material.

The device 1 may include a filter 17, which may be used for purifying the gas from particles and microorganisms. The filter 17 can be arranged on the supply conduit 2.

The device 1 may further include a humidifying member 18 for humidifying the gas to be supplied. The humidifying member 18 is connected to the supply conduit 2 and used to prevent the tissue in the operational space P from drying.

The device 1 may further comprise a cooling member 19 for cooling the gas, which may be located before or after the humidifying member 18 on the supply conduit 2. The density of gases is increased by cooling the gases. The cooler, heavier gas may displace the air in the operational space P more easily.

Also included on or in the supply conduit 2 may be a supply member 20 for the supply of additional components such as medicaments, for example anti-coagulants, hormones, tissue factors, antibiotics and anti-viral drugs. In addition, it is to be noted that the device 1 may include a heating member on the supply conduit 2 for heating the gas to be supplied.

The gas conduit 2 may also comprise a valve 21 by which the gas supply to the body 5 is adjustable. For example, the valve 21 is controlled with the aid of a control member 22 connected to the valve 21. The control member 22 may in turn be connected to a gas-sensing member 23, which is arranged to sense the concentration of the supplied gas or air in the area in question. With the aid of such a sensing, the gas supplied to the area may be controlled in for example such a way that if an increase in air concentration is determined, the gas supplied is also increased or if the concentration of air in the area exceeds a predetermined level, the gas supply is increased.

The gas source 3 may contain substantially pure carbon dioxide. However, a mixture of carbon dioxide and oxygen may be used as well. In one embodiment the carbon dioxide gas is mixed with 0 to 22% oxygen gas. Further, the gas may also comprise various additional components in the form of gases, liquids or particles, for instance disinfectant gases. It is also possible for the gas to comprise various medicaments such as anti-coagulants, hormones, tissue factors, antibiotics and anti-viral drugs. Another possible gas would be pure air, which may be a desired gas in certain medical cases.

The device 1 may be used for the treatment and/or prevention of infections in an open inner portion of a mammal. The device 1 may be used for the prevention of growth of microorganisms in an open inner portion of a mammal. The device 1 may even be used for the treatment of infections in an open inner portion of a mammal outside of surgery such as in situations with open skin wounds. In these embodiments, the bacteriostatic properties of carbon dioxide may be combined with the supply of antibacterial or antiviral medicaments.

The device 1 may further be used for the prevention of embolism in a mammal. This may especially be relevant for heart surgeries.

The present invention is not limited to the embodiments disclosed but may be varied and modified within the scope of the claims.

For instance, the body 5 may be heparinised so that blood or liquids will not, or at least to a lesser extend, block the open cells of the body 5.

The device 1 of the present invention will create a clean gas atmosphere locally at a surface or in a cavity and may be used in other industries such as mounting, soldering, packaging and electronic/computer industry. Different types of gases or mixtures of gases may be relevant for the different industries.

The invention claimed is:

1. A device for the supply of a gas from a gas source to an operational space configured to adjoin a temporarily open inner portion of a mammal during surgical operations, wherein the device comprises:
   a supply conduit, which connects to the gas source and includes an outlet end;
   a body having at least partly an annular shape extending along a circumferential path around a center axis, the body surrounding the operational space and having an inner side facing the operational space, an outer side, an interior channel extending in parallel with the circumferential path, and an opening to allow the gas to enter the interior channel of the body from the supply conduit;

a stiffening member made of a plastically deformable material, wherein the stiffening member extends in parallel with the circumferential path of the body and bends to any suitable shape to enable the body to be adapted to the specific body part of the mammal to be operated, and wherein the body is manufactured of foam rubber-like material having a large number of open cells functioning as supply nozzles so that the gas passes from the interior channel through the foam rubber-like material and through the inner side of the body, thereby supplying a substantially laminar, continuous gas stream into the operational space to form a gas cushion in the operational space, and a pliable cover member that covers the outer side of the body of the foam rubber-like material to direct the gas from the interior channel of the body inwards towards the open inner portion of the mammal, wherein the pliable cover member includes an outer surface and a passage extending through the outer surface and communicating with the supply conduit and the opening of the body, wherein the pliable cover member covers the entire outer side of the body, and wherein the outer side of the body of the foam rubber-like material is directly attached to said outer surface of the pliable cover member.

2. The device according to claim 1, wherein the pliable cover member includes a sleeve, which extends outwardly away from the body and is connected to the outlet end, said passage extending through the sleeve.

3. The device according to claim 1, wherein the body is substantially circular in a radial section with respect to the center axis.

4. The device according to claim 1, wherein the stiffening member enables plastic deformation of the annular shape of the body to adapt to positioning of the operational space in or at various body parts of the mammal.

5. The device according to claim 1, wherein the stiffening member is embedded in the body.

6. The device according to claim 1, wherein the stiffening member is a metal wire.

7. The device according to claim 1, wherein the foam rubber-like material includes poly-urethane foam.

8. The device according to claim 1, further comprising at least one attachment member configured to hold the device adjoined to the open inner portion during surgical operations.

9. The device according to claim 1, further comprising a draping sheet is-attached to the body.

10. The device according to claim 1, wherein the gas is carbon dioxide.

11. Use of the device according to claim 1, for the treatment and/or prevention of infections in an open inner portion of a mammal.

12. The device according to claim 1, wherein the pliable cover member covers part of an inner side of the body.

* * * * *